United States Patent [19]
Curran et al.

[11] 4,159,268
[45] Jun. 26, 1979

[54] 3-CHROMONECARBOXAMIDO DERIVATIVES OF PENICILLINS

[75] Inventors: William V. Curran, Pearl River; Adma S. Ross, Suffern, both of N.Y.

[73] Assignee: American Cyanamid Company, Stamford, Conn.

[21] Appl. No.: 889,679

[22] Filed: Mar. 24, 1978

[51] Int. Cl.$^2$ .................. C07D 499/68; C07D 499/70
[52] U.S. Cl. .................................. 260/239.1; 424/271
[58] Field of Search ...................... 260/239.1; 424/271

[56] References Cited
U.S. PATENT DOCUMENTS

| | | | |
|---|---|---|---|
| 3,433,784 | 3/1969 | Long et al. | 260/239.1 |
| 3,939,150 | 2/1976 | Murakami et al. | 260/239.1 |
| 3,951,952 | 4/1976 | Hamanaka et al. | 260/239.1 |
| 3,954,734 | 5/1976 | Doub et al. | 260/239.1 |
| 4,005,075 | 1/1977 | Yamada et al. | 260/239.1 |

*Primary Examiner*—Gerald A. Schwartz
*Attorney, Agent, or Firm*—Edward A. Conroy, Jr.

[57] ABSTRACT

This disclosure describes compounds of the class of 6-[D-α-(substituted-chromone-3-carboxamido)-phenylacetamido]-penicillanic acids which possess antimicrobial activity.

10 Claims, No Drawings

3-CHROMONECARBOXAMIDO DERIVATIVES OF PENICILLINS

BRIEF SUMMARY OF THE INVENTION

This invention relates to new derivatives of 6-aminopenicillanic acid and, more particularly, is concerned with novel compounds which may be represented by the following structural formula:

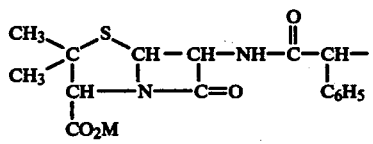

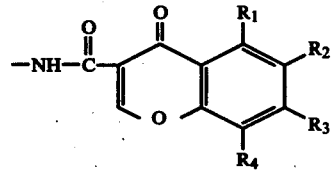

wherein $R_1$ and $R_4$ are each individually selected from the group consisting of hydrogen, nitro and alkyl having up to 4 carbon atoms; $R_2$ and $R_3$ are each individually selected from the group consisting of hydrogen, hydroxy, alkoxy having up to 4 carbon atoms, alkyl having up to 4 carbon atoms, phenyl, nitro, fluoro, chloro, bromo, alkanoyloxy having up to 4 carbon atoms and alkoxycarbonyloxy having up to 4 carbon atoms; $R_1$ and $R_2$ taken together, $R_2$ and $R_3$ taken together, and $R_3$ and $R_4$ taken together are each butadienylene; and M is hydrogen or a pharmaceutically acceptable non-toxic cation with the proviso that at least two of $R_1$, $R_2$, $R_3$ and $R_4$ must be hydrogen.

DETAILED DESCRIPTION OF THE INVENTION

Suitable alkyl and alkoxy groups contemplated by the present invention are, for example, methyl, ethyl, isopropyl, sec-butyl, methoxy, ethoxy, n-propoxy, isobutoxy, and the like. Appropriate alkanoyloxy and alkoxycarbonyloxy groups may be, for example, propionyloxy, isobutyryloxy, methoxycarbonyloxy, isopropoxycarbonyloxy, etc. The pharmacologically acceptable cations embraced by M in the above general formula include, for example, the non-toxic metal cations such as the sodium ion, potassium ion, calcium ion, magnesium ion, as well as the organic amine cations such as the tri(lower alkyl)amine cations (e.g., triethylamine), procaine, and the like.

The novel compounds of the present invention may be readily prepared in the free acid form (M is hydrogen) by condensing ampicillin with a chromone-3-carboxylic acid derivative of the formula

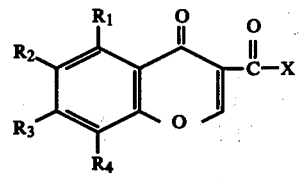

wherein $R_1$, $R_2$, $R_3$ and $R_4$ are as hereinabove defined and X is chloro or bromo as in an acid halide, or the moiety —O—CO—OC$_2$H$_5$ as in a mixed anhydride from ethyl chloroformate, or the moiety —O—C(=N-cyclohexyl)NH-cyclohexyl as in a dicyclohexylcarbodiimide mediated reaction, or an azide function, or an azolide formed from carbonyldiimidazole. This acylation of ampicillin is best performed in an inert solvent such as tetrahydrofuran, dioxane, methylene chloride or chloroform (or mixtures thereof) at from ice bath temperature (about 0° C.) to room temperature (about 35° C.). The reaction is preferably carried out in the presence of an acid acceptor such as N-methylmorpholine, triethylamine or soda ash and over a period of time of a few hours or more. The acylating agents may be prepared by methods well known in the art from the corresponding acids (X is hydroxy). Thus, an acid may be treated with a thionyl halide or oxalyl halide, if desired in the presence of dimethylformamide, to yield the corresponding acyl halides (X is chloro or bromo), which can be converted to the acyl azides (X is $N_3$) by treatment with sodium azide.

The novel compounds of the present invention are biologically active and have been found to possess antibacterial activity. As indicated, they are useful antimicrobial agents and have broadspectrum antimicrobial activity in vitro against standard laboratory microorganisms used to screen for activity against pathogens. The antibacterial spectrum of typical compounds of the present invention, representing the concentration required to inhibit the growth of various typical bacteria, was determined in a standard manner by the agar-dilution streak-plate technique. A Steers multiple inocula replicator was employed with incubation at 37° C. for 18 hours in conventional nutrient agar. The results are set forth in Table I below expressed as the minimal inhibitory concentration in micrograms per milliliter.

TABLE I

| Compound | Pseudo. aeruginosa USC 76-13 | Klebsiella pneum. MA 75-2 | Entero. clocae OSU 75-2 | Proteus mirabilis OSU 75-3 | Proteus morganii K 72 | Escher. coli W 75-1 | Staph. aureus OSU 75-2 |
| --- | --- | --- | --- | --- | --- | --- | --- |
| 6-[D-α-(Chromone-3-carboxamido)phenylacetamido]penicillanic acid | 4 | 16 | 16 | 2 | 8 | 4 | 0.25 |
| 6-[D-α-(6-Methylchromone-3--carboxamido)phenylacetamido]-penicillanic acid | 2 | 2 | 4 | 0.25 | 2 | 1 | 0.12 |
| 6-[D-α-(7,8-Benzochromone-3--carboxamido)phenylacetamido]-penicillanic acid | 4 | 4 | 4 | 1 | 1 | 2 | 0.25 |
| 6-[D-α-(6,7-Dimethylchromone-3-carboxamido)phenylacetamido]penicillanic acid | 2 | 2 | 2 | 0.25 | 1 | 1 | 0.12 |
| 6-[D-α-(7-Methoxychromone-3--carboxamido)phenylacetamido]- | 4 | 2 | 4 | 0.5 | 4 | 2 | 0.25 |

TABLE I-continued

| Compound | Pseudo. aeruginosa USC 76-13 | Klebsiella pneum. MA 75-2 | Entero. clocae OSU 75-2 | Proteus mirabilis OSU 75-3 | Proteus morganii K 72 | Escher. coli W 75-1 | Staph. aureus OSU 75-2 |
|---|---|---|---|---|---|---|---|
| penicillanic acid | | | | | | | |
| 6-[D-α-(5,7-Dimethylchromone-3-carboxamido)phenylacetamido]penicillanic acid | 8 | 4 | — | 0.25 | 1 | 1 | ≦0.06 |
| 6-[D-α-(6-Ethylchromone-3-carboxamido)phenylacetamido]penicillanic acid | 2 | 1 | — | 0.12 | 1 | 1 | ≦0.06 |
| 6-[D-α-(6-Phenylchromone-3-carboxamido)phenylacetamido]penicillanic acid | 4 | 4 | 2 | 0.5 | 4 | 2 | 0.25 |
| 6-[D-α-(7-Hydroxychromone-3-carboxamido)phenylacetamido]penicillanic acid | 8 | 8 | 4 | 1 | 16 | 4 | 0.12 |
| 6-[D-α-(7-Acetyloxychromone-3-carboxamido)phenylacetamido]penicillanic acid | 8 | 8 | 4 | 1 | 8 | 4 | 0.12 |
| 6-[D-α-(7-Ethoxycarbonyloxy-3-carboxamido)phenylacetamido]penicillanic acid | 16 | 32 | 8 | 4 | 32 | 16 | 0.5 |
| 6-[D-α-(7-Methylchromone-3-carboxamido)phenylacetamido]penicillanic acid | 4 | 8 | 4 | 1 | 8 | 4 | 0.25 |
| 6-[D-α-(6-Acetyloxychromone-3-carboxamido)phenylacetamido]penicillanic acid | 4 | 8 | 2 | 1 | 8 | 4 | 0.12 |
| 6-[D-α-(6-Fluorochromone-3-carboxamido)phenylacetamido]penicillanic acid | 16 | 32 | 8 | 1 | 16 | 16 | <0.06 |
| 6-[D-α-(6-Ethoxycarbonyloxy-3-carboxamido)phenylacetamido]penicillanic acid | 8 | 16 | 4 | 1 | 16 | 8 | 0.25 |
| 6-[D-α-(6-Hydroxychromone-3-carboxamido)phenylacetamido]penicillanic acid | 2 | 4 | 4 | 2 | 4 | 4 | 0.25 |
| 6-[D-α-(6-Nitrochromone-3-carboxamido)phenylacetamido]penicillanic acid | >128 | 128 | 64 | 1 | 128 | 8 | <0.06 |
| 6-[D-α-(5-Nitro-6-methylchromone-3-carboxamido)phenylacetamido]penicillanic acid | 32 | 16 | 8 | 1 | 16 | 8 | 0.25 |
| 6-[D-α-(7-Ethoxycarbonyloxy-8-nitrochromone-3-carboxamido)phenylacetamido]penicillanic acid | 128 | 64 | 32 | 2 | >128 | 16 | 0.12 |
| 6-[D-α-(7-Hydroxy-8-nitrochromone-3-carboxamido)phenylacetamido]penicillanic acid | >128 | 128 | 64 | 2 | >128 | 16 | 0.12 |
| Carbenicillin | 32 | >128 | 32 | 1 | 128 | 8 | 1 |
| Ampicillin | >128 | 16 | >128 | 0.25 | >128 | 1 | 0.12 |
| 7-{[N-(6,7-dimethyl-4-chromon-3-carboxyl)-2-phenylglycyl]amino}cephem-3-methyl-4-carboxylic acid | 128 | 32 | 32 | 16 | 64 | 16 | 2 |

A preferred embodiment of the present invention may be represented by the following structural formula:

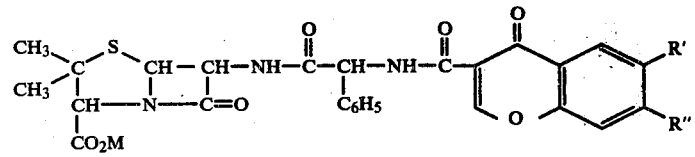

wherein R' and R" are each individually selected from the group consisting of hydrogen, hydroxy, methyl, ethyl, methoxy, ethoxy, fluoro, acetyloxy, propionyloxy, methoxycarbonyloxy and ethoxycarbonyloxy and R' and R" taken together is butadienylene and M is hydrogen or a pharmacologically acceptable cation.

The invention will be described in greater detail in conjunction with the following specific examples.

EXAMPLE 1

6-[D-α-(Chromone-3-carboxamido)phenylacetamido]-penicillanic acid

A 0.194 ml. portion of ethyl chloroformate is added dropwise to a stirred solution of 389 mg. of chromone-3-carboxylic acid [A. Nohara, et al., Chem. Pharm. Bull., 22, 2959 (1974)] and 0.234 ml. of N-methylmorpholine in 45 ml. of dioxane and 10 ml. of acetone, immersed in an ice bath. After stirring for 15 minutes, an additional 0.234 ml. of N-methylmorpholine is added followed by 807 mg. of ampicillin trihydrate. The mixture is stirred for 1.5 hours in the ice bath, then a cold solution of 3 ml. of saturated sodium bicarbonate in 35 ml. of water is added. The mixture is extracted with 150 ml. of cold ethyl acetate. The aqueous layer is acidified to pH 2 with hydrochloric acid and extracted with 100 ml. followed by 50 ml. of ethyl acetate. The combined ethyl acetate extracts are washed with 25 ml. of water, dried over magnesium sulfate and evaporated to dryness in vacuo. The residue is triturated to a solid in a mixture of ether and hexane, giving the desired derivative, I.R. 5.62μ (β-lactam carbonyl).

EXAMPLE 2

6-[D-α-(6-Methylchromone-3-carboxamido)-phenylacetamido]penicillanic acid

A stirred solution of 2.65 g. of 6-methylchromone-3-carboxylic acid in 300 ml. of dioxane and 65 ml. of acetone is cooled in a salt-ice bath and 1.8 ml. of triethylamine and 1.25 ml. of ethylchloroformate are added. The mixture is stirred at −5° to 0° C. for 30 minutes and then 1.8. ml. of triethylamine and 5.24 g. of ampicillin trihydrate are added. This suspension is stirred for one hour at 0° to 5° C. and then treated with 230 ml. of cold water plus 20 ml. of saturated sodium bicarbonate. The cold aqueous solution is extracted with 1.3 liters of ethyl acetate, acidified to pH 2 with concentrated hydrochloric acid and the product is extracted with three 500 ml. portions of ethyl acetate. The combined ethyl acetate extracts are washed with saturated sodium chloride, dried over magnesium sulfate, evaporated to an oil and precipitated with hexane. The desired product is collected by filtration and has an I.R. 5.62μ (β-lactam carbonyl).

EXAMPLE 3

6-[D-α-(7,8-Benzochromone-3-carboxamido)-phenylacetamido]penicillanic acid

A 0.48 g. portion of 7,8-benzochromone-3-carboxylic acid is reacted with 0.195 ml. of ethyl chloroformate, twice with 0.28 ml. of triethylamine and 0.8 g. of ampicillin trihydrate according to the procedure of Example 2, giving the desired product, I.R. 5.61μ (β-lactam carbonyl).

EXAMPLE 4

6-[D-α-(6,7-Dimethylchromone-3-carboxamido)-phenylacetamido]penicillanic acid

A 0.44 g. portion of 6,7-dimethylchromone-3-carboxylic acid is reacted with 0.195 ml. of ethyl chloroformate, twice with 0.28 ml. of triethylamine and 0.8 g. of ampicillin trihydrate according to the procedure of Example 2, giving the desired product, I.R. 5.62μ (β-lactam carbonyl).

EXAMPLE 5

6-[D-α-(7-Methoxychromone-3-carboxamido)-phenylacetamido]penicillanic acid

A 0.11 g. portion of 7-methoxychromone-3-carboxylic acid is reacted with 0.10 ml. of ethyl chloroformate, twice with 0.14 ml. of triethylamine and 0.2 g. of ampicillin trihydrate as described in Example 2, giving the desired product, I.R. 5.62μ (β-lactam carbonyl).

EXAMPLE 6

6-[D-α-(5,7-Dimethylchromone-3-carboxamido)-phenylacetamido]penicillanic acid

A 0.218 g. portion of 5,7-dimethylchromone-3-carboxylic acid is reacted with 0.095 ml. of ethyl chloroformate, twice with 0.14 ml. of triethylamine and 0.4 g. of ampicillin trihydrate as described in Example 2 giving the desired product, I.R. 5.62μ (β-lactam carbonyl).

EXAMPLE 7

6-[D-α-(6-Ethylchromone-3-carboxamido)-phenylacetamido]penicillanic acid

A 1.21 g. portion of 6-ethylchromone-3-carboxylic acid [A. Nohara, et al., Chem. Pharm. Bull., 22, 2959 (1974)] is reacted with 0.59 ml. of ethyl chloroformate, twice with 0.84 ml. of triethylamine and 2.4 g. of ampicillin trihydrate as described in Example 2, giving the desired product, I.R. 5.60μ (β-lactam carbonyl).

EXAMPLE 8

6-[Dα-(6-Phenylchromone-3-carboxamido)-phenylacetamido]penicillanic acid

A 0.266 g. portion of 6-phenylchromone-3-carboxylic acid is reacted with 0.095 ml. of ethyl chloroformate, twice with 0.14 ml. of triethylamine and 0.4 g. of ampicillin trihydrate as described in Example 2, giving the desired product, I.R. 5.62μ (β-lactam carbonyl).

EXAMPLE 9

6-[D-α-(7-Hydroxychromone-3-carboxamido)-phenylacetamido]penicillanic acid

A 0.206 g. portion of 7-hydroxychromone-3-carboxylic acid is reacted with 0.095 ml. of ethyl chloroformate, twice with 0.14 ml. of triethylamine and 0.4 g of ampicillin trihydrate as described in Example 2, giving the desired product, I.R. 5.60μ (β-lactam carbonyl).

EXAMPLE 10

6-[D-α-(7-Acetyloxychromone-3-carboxamido)-phenylacetamido]penicillanic acid

A 0.232 g. portion of 7-acetyloxychromone-3-carboxylic acid is reacted with 0.095 ml. of ethyl chloroformate, twice with 0.14 ml. of triethylamine and 0.4 g. of ampicillin trihydrate as described in Example 2, giving the desired product, I.R. 5.65μ (β-lactam carbonyl plus ester carbonyl).

EXAMPLE 11

6-[D-α-(7-Ethoxycarbonyloxy-3-carboxamido)-phenylacetamido]penicillanic acid

A 0.206 g. portion of 7-hydroxychromone-3-carboxylic acid, is reacted with 0.195 ml. of ethyl chloroformate, a 0.028 ml. and a 0.14 ml. portion of triethylamine and 0.4 g. of ampicillin trihydrate as described in Example 2, giving the desired product, I.R. 5.60μ (β-lactam carbonyl plus ethoxycarbonyl).

EXAMPLE 12

6-[D-α-(7-Methylchromone-3-carboxamido)-phenylacetamido]penicillanic acid

A 0.408 g. portion of 7-methylchromone-3-carboxylic acid is reacted with 0.195 ml. of ethyl chloroformate, twice with 0.28 ml. of triethylamine and 0.81 g. of ampicillin trihydrate as described in Example 2, giving the desired product, I.R. 5.61μ (β-lactam carbonyl).

EXAMPLE 13

6-[D-α-(6-Acetyloxychromone-3-carboxamido)-phenylacetamido]penicillanic acid

A 0.232 g. portion of 6-acetyloxychromone-3-carboxylic acid [A. Nohara, et al., Chem. Pharm. Bull., 22, 2959 (1974)] is reacted with 0.095 ml. of ethyl chloroformate, twice with 0.14 ml. of triethylamine and 0.4 g. of ampicillin trihydrate as described in Example 2, giving the desired product, I.R. 5.60–5.66μ (β-lactam carbonyl plus acetoxy carbonyl).

EXAMPLE 14

6-[D-α-(6-Fluorochromone-3-carboxamido)-phenylacetamido]penicillanic acid

A 0.21 g. portion of 6-fluorochromone-3-carboxylic acid is reacted with 0.095 ml. of ethyl chloroformate, twice with 0.028 ml. of triethylamine and 0.4 g. of ampicillin trihydrate as described in Example 2, giving the desired product, I.R. 5.61μ (β-lactam carbonyl).

EXAMPLE 15

6-[D-α-(6-Ethoxycarbonyloxy-3-carboxamido)-phenylacetamido]penicillanic acid

A 0.21 g. portion of 7-hydroxychromone-3-carboxylic acid is reacted with 0.195 ml. of ethyl chloroformate, 0.28 ml. and 0.14 ml. portions of triethylamine and 0.4 g. of ampicillin trihydrate as described in Example 2, giving the desired product, I.R. 5.60–5.67μ (β-lactam carbonyl).

EXAMPLE 16

6-[D-α-(6-Hydroxychromone-3-carboxamido)-phenylacetamido]penicillanic acid

A stirred solution of 185 mg. of 6-hydroxychromone-3-carboxyl chloride in a mixture of 45 ml. of dioxane and 5 ml. of acetone is cooled in an ice-salt bath, treated with 0.28 ml. of triethylamine and 0.4 g. of ampicillin trihydrate and stirred first at 0° to 5° C. for 30 minutes and then at 5° to 10° C. for 90 minutes. The reaction mixture is poured into 50 ml. of ice water and saturated sodium bicarbonate is added to a pH of 7.8. The mixture is extracted with two 100 ml. portions of ethyl acetate. The aqueous layer is acidified to pH 2 with concentrated hydrochloric acid and the product is extracted with three 100 ml. portions of ethyl acetate. The ethyl acetate extracts are combined, washed with saturated aqueous sodium chloride, dried over magnesium sulfate, evaporated to an oil and precipitated with hexane. The desired product is collected by filtration, I.R. 5.62μ (β-lactam carbonyl).

EXAMPLE 17

6-[D-α-(6-Nitrochromone-3-carboxamido)-phenylacetamido]penicillanic acid

A 0.235 g. portion of 6-nitrochromone-3-carboxylic acid is reacted with 0.095 ml. of ethyl chloroformate, twice with 0.14 ml. of triethylamine and 0.4 g. of ampicillin trihydrate as described in Example 2, giving the desired product, I.R. 5.63μ (β-lactam carbonyl).

EXAMPLE 18

6-[D-α-(5-Nitro-6-methylchromone-3-carboxamido)-phenylacetamido]penicillanic acid A 0.25 g. portion of 5-nitro-6-methylchromone-3-carboxylic acid is reacted with 0.095 ml. of ethyl chloroformate, twice with 0.14 ml. of triethylamine and 0.4 g. of ampicillin trihydrate as described in Example 2, giving the desired product, I.R. 5.64μ (β-lactam carbonyl).

EXAMPLE 19

6-[D-α-(7-Ethoxycarbonyloxy-8-nitrochromone-3-carboxamido)phenylacetamido]penicillanic acid A 0.25 g. portion of 7-hydroxy-8-nitrochromone-3-carboxylic acid is reacted with 0.195 ml. of ethyl chloroformate, 0.28 ml. and 0.14 ml. of triethylamine and 0.4 g. of ampicillin trihydrate as described in Example 2, giving the desired product, I.R. 5.64μ (β-lactam carbonyl and ethoxycarbonyl).

EXAMPLE 20

6-[D-α-(7-Hydroxy-8-nitrochromone-3-carboxamido)-phenylacetamido]penicillanic acid A 0.25 g. portion of 7-hydroxy-8-nitrochromone-3-carboxylic acid is reacted with 0.095 ml. of ethyl chloroformate, twice with 0.14 ml. of triethylamine and 0.4 g. of ampicillin trihydrate as described in Example 2, giving the desired product, I.R. 5.62μ (β-lactam carbonyl).

EXAMPLE 21

7-{[N-(6,7-dimethyl-4-chromon-3-carboxyl)-2-phenylglycyl]amino}cephem-3-methyl-4-carboxylic acid A suspension of 218 mg. of 6,7-dimethyl-4-chromone-3-carboxylic acid in 22 ml. dioxane plus 5 ml. acetone was stirred and treated at 0°–5° C. with 0.14 ml. of triethylamine and 0.095 ml. of ethyl chloroformate. The reaction mixture was stirred at 0°–5° C. for 30 minutes, and 0.14 ml. of triethylamine and 400 ml. of cephalexin were added. After stirring for one hour, 20 ml. of water and 1.5 ml. of saturated NaHCO₃ were added. Extraction with ethyl acetate was followed by acidification of the aqueous layer to pH2. The product was extracted into ethyl acetate and the ethyl acetate was washed with saturated NaCl, dried over MgSO₄ and evaporated. The residue was washed with ether and hexane to give 380 mg. of product.

We claim:
1. A compound of the formula:

$$\begin{array}{c}CH_3\\CH_3\end{array}C\begin{array}{c}S\\\\CH\end{array}\begin{array}{c}CH-CH-NH-C-CH-\\|\ \ \ \ \ \ \ \ \ \ \ \ \ \ \ \ \ \ \ \ \ \ \ \ \|\ \ \ \ \ \ |\\N---C=O\ \ \ \ \ \ \ \ \ \ \ \ \ C_6H_5\\|\\CO_2M\end{array}$$

[chromone structure with substituents $R_1$, $R_2$, $R_3$, $R_4$ attached to –NH–C(=O)– group]

wherein $R_1$ and $R_4$ are each individually selected from the group consisting of hydrogen, nitro and alkyl having up to 4 carbon atoms; $R_2$ and $R_3$ are each individually selected from the group consisting of hydrogen, hydroxy, alkoxy having up to 4 carbon atoms, alkyl having up to 4 carbon atoms, phenyl, nitro, fluoro, chloro, bromo, alkanoyloxy having up to 4 carbon atoms and alkoxycarbonyloxy having up to 4 carbon atoms; $R_1$ and $R_2$ taken together, $R_2$ and $R_3$ taken together, and $R_3$ and $R_4$ taken together are each butadienylene; and M is hydrogen or a pharmaceutically acceptable non-toxic cation with the proviso that at least two of $R_1$, $R_2$, $R_3$ and $R_4$ must be hydrogen.

2. The compound according to claim 1 wherein $R_1$, $R_2$, $R_3$, $R_4$ and M are each hydrogen; 6-[D-α-(chromone-3-carboxamido)phenylacetamido]penicillanic acid.

3. The compound according to claim 1 wherein $R_3$, $R_4$ and M are each hydrogen and $R_1$ and $R_2$ taken together is butadienylene; 6-[D-α-(5,6-benzochromone-3-carboxamido)phenylacetamido]penicillanic acid.

4. The compound according to claim 1 wherein $R_1$, $R_4$ and M are each hydrogen and $R_2$ and $R_3$ taken together is butadienylene; 6-[D-α-(6,7-benzochromone-3-carboxamido)phenylacetamido]penicillanic acid.

5. The compound according to claim 1 wherein $R_1$, $R_2$, $R_4$ and M are each hydrogen and $R_3$ is fluoro; 6-[D-α-(7-fluorochromone-3-carboxamido)-phenylacetamido]penicillanic acid.

6. The compound according to claim 1 wherein $R_1$, $R_4$ and M are each hydrogen and $R_2$ and $R_3$ are both hydroxy; 6-[D-α-(6,7-dihydroxychromone-3-carboxamido)phenylacetamido]penicillanic acid.

7. The compound according to claim 1 wherein $R_1$, $R_3$, $R_4$ and M are each hydrogen and $R_2$ is methoxy; 6-[D-α-(6-methoxychromone-3-carboxamido)-phenylacetamido]penicillanic acid.

8. The compound according to claim 1 wherein $R_1$, $R_2$, $R_4$ and M are each hydrogen and $R_3$ is ethyl; 6-[D-α-(7-ethylchromone-3-carboxamido)phenylacetamido]-penicillanic acid.

9. The compound according to claim 1 wherein $R_1$, $R_3$, $R_4$ and M are each hydrogen and $R_2$ is methoxycarbonyloxy; 6-[D-α-(6-methoxycarbonyloxychromone-3-carboxamido)phenylacetamido]penicillanic acid.

10. The compound according to claim 1 wherein $R_1$, $R_2$, $R_4$ and M are each hydrogen and $R_3$ is propionyloxy; 6-[D-α-(7-propionyloxychromone-3-carboxamido)phenylacetamido]penicillanic acid.

* * * * *